(12) United States Patent
Hoffmann et al.

(10) Patent No.: US 9,096,621 B2
(45) Date of Patent: *Aug. 4, 2015

(54) METHOD FOR PREPARING POLY(HYDROXYMETHYL)-FUNCTIONAL SILOXANES AND SILICA GELS

(75) Inventors: Florian Hoffmann, Munich (DE); Sascha Andre Erhardt, Biberach (DE); Bernhard Rieger, Elchingen (DE); Juergen Stohrer, Pullach (DE)

(73) Assignee: Wacker Chemie AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/238,510

(22) PCT Filed: Jul. 18, 2012

(86) PCT No.: PCT/EP2012/064053
§ 371 (c)(1),
(2), (4) Date: Feb. 12, 2014

(87) PCT Pub. No.: WO2013/023862
PCT Pub. Date: Feb. 21, 2013

(65) Prior Publication Data
US 2014/0213808 A1    Jul. 31, 2014

(30) Foreign Application Priority Data
Aug. 12, 2011    (DE) .................. 10 2011 080 888

(51) Int. Cl.
*C08G 77/04*    (2006.01)
*C07F 7/18*    (2006.01)
*C08G 77/14*    (2006.01)
*C08G 77/10*    (2006.01)

(52) U.S. Cl.
CPC ............ *C07F 7/1872* (2013.01); *C07F 7/1804* (2013.01); *C08G 77/14* (2013.01); *C08G 77/10* (2013.01)

(58) Field of Classification Search
USPC .................................................... 528/10, 37
See application file for complete search history.

(56) References Cited

U.S. PATENT DOCUMENTS

| 2,833,802 | A | * | 5/1958 | Merker ..................... 556/440 |
| 2,837,550 | A | | 6/1958 | Prober |
| 3,324,161 | A | | 6/1967 | Simmler |
| 3,446,830 | A | | 5/1969 | Niederprum et al. |
| 3,481,963 | A | | 12/1969 | Simmler et al. |
| 3,879,433 | A | | 4/1975 | Omietanski et al. |
| 5,371,262 | A | | 12/1994 | Arkles |
| 6,310,110 | B1 | | 10/2001 | Markowitz et al. |
| 8,822,621 | B2 | * | 9/2014 | Daiss et al. ..................... 528/40 |
| 2004/0073031 | A1 | | 4/2004 | Schaefer et al. |
| 2007/0269662 | A1 | | 11/2007 | Lopez et al. |
| 2008/0268162 | A1 | | 10/2008 | Borovik et al. |
| 2012/0220793 | A1 | | 8/2012 | Daiss et al. |
| 2013/0018200 | A1 | | 1/2013 | Daiss et al. |

FOREIGN PATENT DOCUMENTS

| DE | 879839 | 6/1953 |
| DE | 1213406 | 3/1966 |
| DE | 1227456 B | 10/1966 |
| DE | 1233395 B | 2/1967 |
| DE | 1236505 | 3/1967 |
| DE | 4407437 A1 | 9/1994 |
| DE | 10044635 A1 | 4/2002 |
| DE | 10109842 A1 | 10/2002 |
| DE | 102009046254 A1 | 5/2011 |
| DE | 102010003108 A1 | 9/2011 |
| GB | 1121265 | 7/1968 |
| JP | 2004-527609 A | 9/2004 |
| JP | 2007122029 A | 5/2007 |
| JP | 2007182555 A2 | 7/2007 |
| JP | 2008292712 A | 12/2008 |
| JP | 2011154067 A | 8/2011 |
| JP | 2013-509465 A | 3/2013 |
| WO | 02/070586 A1 | 9/2002 |

OTHER PUBLICATIONS

H. Du et al., Journal of Colloid and Interface Science, 340 (2009) "A facile synthesis of highly water-soluble, core-shell organo-silica nanoparticles with controllabe size via sol-gel process," pp. 202-208.
J. Am. Chem. Soc. 77 (1955) p. 5180: "Grignardization of chloromethylsiloxnes and subsequent oxidation and hydrolysis."

* cited by examiner

*Primary Examiner* — Sudhakar Katakam
*Assistant Examiner* — Pancham Bakshi
(74) *Attorney, Agent, or Firm* — Brooks Kushman P.C.

(57) ABSTRACT

Hydroxymethyl-functional siloxanes and silica gels are prepared by reacting a siloxacycle having at least one unit of the formula $[SiR^2(OR^3)-CH_2-O]_n$ with water, optionally in the presence of a hydrolyzable silane.

13 Claims, No Drawings

METHOD FOR PREPARING POLY(HYDROXYMETHYL)-FUNCTIONAL SILOXANES AND SILICA GELS

CROSS-REFERENCE TO RELATED APPLICATIONS

This application is the U.S. National Phase of PCT Appln. No. PCT/EP2012/064053 filed Jul. 18, 2012, which claims priority to German application DE 10 2011 080 888.4 filed Aug. 12, 2011, the disclosures of which are incorporated in their entirety by reference herein.

BACKGROUND OF THE INVENTION

1. Field of the Invention

The present invention relates to a method for preparing poly(hydroxymethyl)-functional siloxanes and to poly(hydroxymethyl)-functional siloxanes.

2. Description of the Related Art

Poly(hydroxyalkyl)-functional siloxanes, including polysiloxanes, polysiloxane resins and organofunctional silica gels, incorporate as structural elements multiple units of the formula

$$(\text{siloxane-O})_{1+x}\text{SiR}^i{}_{2-x}\text{-R}^{ii}\text{—OH},$$

where $R^i$ is an alkyl residue or an aryl residue, generally a methyl residue, $R^{ii}$ is a hydrocarbon residue, which may comprise or be substituted with heteroatoms, and which is attached to the silicon atom in the group $\text{SiR}^i{}_{2-x}$ via a carbon atom, and $x=0$, 1 or 2.

Siloxanes, polysiloxanes, polysiloxane resins and organofunctional silica gels are together referred to below as "siloxanes". "Heteroatom" is understood to mean every atom except carbon and hydrogen, in particular nitrogen, oxygen, halogen, silicon, phosphorus and sulfur.

The presence of $R^{ii}$ between the silicon atom and the depicted OH group has the effect that the bond attaching the OH group to the siloxane skeleton is stable to hydrolysis. If the OH group is reacted with other compounds, e.g. in polyaddition reactions with, for example, isocyanates or in polycondensation reactions with, for example, carboxylic acids, the bond attaching the resulting products to the siloxane skeleton will likewise be stable to hydrolysis.

The group $R^{ii}$ is in this case a structure-conferring factor, which co-determines not only the properties of the poly(hydroxyalkyl)-functional siloxane but also the properties of the conversion products. It is especially both the mobility of $R^{ii}$ and the organic character of $R^{ii}$ which influence these properties (e.g. hardness, flammability or hydrophilicity). If, for example, the mobility of $R^{ii}$ and/or the organic character of a poly(hydroxyalkyl)-functional siloxane or the conversion products thereof are to be kept to a minimum, the smallest possible $R^{ii}$ residues are ideal, and the choice of $R^{ii}$ as $CH_2$ is particularly advantageous. A further advantage of this choice for $R^{ii}$ is that small structural units mean lower reaction volumes for the same amount of substance with $R^{ii}$-attached OH groups and hence enhanced space-time yields both in the preparation of poly(hydroxyalkyl)-functional siloxanes and conversion products thereof. The $CH_2$ group is, in this respect, the most efficient solution.

Moreover, the $CH_2$ group is likewise the most advantageous solution when the hydrophilicity of the poly(hydroxyalkyl)-functional siloxane is to be as high as possible. Compared to Si—OH groups, the Si—$CH_2$—OH unit has the advantage that condensation reactions with one another, which alter the Si—O skeleton of the poly(hydroxyalkyl)-functional siloxane, cannot occur. The degree of hydrophilicity can be controlled by the number of hydroxyalkyl residues and can range up to water-solubility. In this manner, siloxanes can be accorded a property which can otherwise only be achieved with difficulty in this substance class.

Poly(hydroxyalkyl)-functional siloxanes, where $R^{ii}$ is equal to $CH_2$, are referred to in the poly(hydroxymethyl)-functional siloxanes below.

Methods for preparing poly(hydroxyalkyl)-functional siloxanes are documented in the literature. U.S. Pat. No. 3,879,433, for example, describes the preparation of poly(hydroxyalkyl)-functional siloxanes by hydrosilylation of hydroxyolefins. However, only hydroxyalkyl groups having at least three carbon atoms are accessible in this manner.

The preparation of poly(hydroxymethyl)-functional siloxanes is possible by acid-catalyzed alcoholysis of corresponding poly(acyloxy)methyl-functional siloxanes (e.g. DE 879839) or (acyloxy)methylsilanes (e.g. DE 1236505), in the latter case combined with cohydrolysis and co-condensation with further silanes.

Additional methods are described for the introduction of terminal or single lateral hydroxymethyl groups into siloxane molecules:

DE 879839: acid- or base-catalyzed equilibration of 1,3-bis(acyloxymethyl)tetramethyldisiloxane with further silanes with simultaneous alcoholytic ester cleavage, U.S. Pat. No. 2,837,550/J. Am. Chem. Soc. 77 (1955) 5180: Grignardization of chloromethylsiloxanes and subsequent oxidation and hydrolysis, DE 1213406: hydroxylation of bromomethylsiloxanes with metal hydroxides, DE 1227456: acid-catalyzed equilibration of 1,3-bis(hydroxymethyl)tetramethyldisiloxane with further silanes, DE 1233395: reductive cleavage of (acyloxy)methylsiloxanes with boranates in the presence of boron trifluoride, DE 102009046254: reaction of terminally OH-functionalized polysiloxanes with cyclic or acyclic alkoxysilanes.

The methods described to date for preparing (hydroxymethyl)-functional siloxanes have multiple disadvantages:

1. Under the reaction conditions described, particularly in the equilibration methods, slight rearrangements of the siloxane skeleton occur such that the methods do not result in defined products (DE 879839, DE 1236505, DE 1213406, DE 1227456, DE 1233395).

2. Grignard compounds are expensive due to the magnesium metal required. The oxidation reaction is strongly exothermic and therefore difficult to manage on an industrial scale and not without hazard. Hydroxymethyl groups, moreover, are only formed in low yield (U.S. Pat. No. 2,837,550).

3. The liberation of the ≡SiCH₂OH groups from the corresponding precursor compounds (e.g. ≡SiCH₂—Oacyl or ≡SiCH₂-halogen) frequently does not proceed quantitatively (DE 879839, U.S. Pat. No. 2,837,550, DE 1236505, DE 1213406, DE 1227456, DE 1233395).

4. Boronates are costly and, also like boron trifluoride, hazardous reagents (DE 1233395).

5. The ≡SiCH₂OH groups formed react further under the reaction conditions (e.g. with HCl to give ≡SiCH₂Cl groups, with acidic catalysts, e.g. sulfuric acid, to give ≡SiCH₂OCH₂Si≡ groups or with hydroxides by cleavage of the Si—C bond of the SiCH₂OH groups to give Si—OH groups) such that the product does not have the theoretically expected number and concentration of ≡SiCH₂OH groups (DE 879839, DE 1236505, DE 1213406, DE 1227456, DE 1233395).

6. Reagent residues and/or catalyst residues in the product frequently lead to rearrangement, cleavage, condensation or equilibration of the siloxane skeleton, such that the properties of hydroxymethyl-functional siloxanes, which were prepared by the methods described to date, frequently change on storage (DE 879839, DE 1236505, DE 1213406, DE 1227456, DE 1233395).

7. The methods provide only terminal, and therefore a limited number of, hydroxymethyl groups (DE 1227456, DE 102009046254).

All this complicates or prevents the preparation of poly(hydroxymethyl)-functional siloxanes and the further processing thereof to give defined conversion products and this applies especially to subsequent reactions of the $SiCH_2OH$ group.

The preparation of poly(hydroxymethyl)-functional silica gels by hydrolysis of hydroxymethyltrialkoxysilanes has been described:

JP 63048364: cohydrolysis with further silanes for surface coating,

DE 4407437: sol-gel hydrolysis for preparing thin layers,

U.S. Pat. No. 6,310,110: emulsion hydrolysis in the presence of surface-active substances having template groups for preparing micro- or nanostructured porous particles, US 2007 0269662: sol-gel hydrolysis for preparing thin membranes, US 2008 0268162: hydrolysis, optionally in the presence of surface-active substances, for surface coating, J. Coll. Interface Sc. 340 (2009) 202-208: sol-gel cohydrolysis with a further silane in the presence of a surface-active substance for preparing particles with corn-shell structure, DE 10044635: cohydrolysis for encapsulating active ingredients.

A common aspect of the methods referred to is that they use an alcoholic solution of a hydroxymethyltrialkoxysilane as starting material. This also comprises condensation products having $Si-CH_2-O-Si$ units in the equilibrium, specifically more so the higher the silane concentration (DE 4407437). This is disadvantageous since complete hydrolysis is no longer ensured at a high degree of condensation, since not all $Si-OR$ or $Si-CH_2-O-Si$ units are accessible to hydrolysis, due to the resulting strong cross-linking and steric shielding. If a high alcohol dilution is employed in order to avoid this issue, this can likewise be disadvantageous since a free choice of silane concentration and solvent is no longer possible. However, these are important parameters for controlling the size and morphology of the resulting silica gel particles.

All this complicates or prevents the preparation of poly(hydroxymethyl)-functional silica gels, particularly having defined structure and morphology, and the further processing thereof to give defined conversion products and this applies especially to subsequent reactions of the $SiCH_2OH$ group.

SUMMARY OF THE INVENTION

An object of the invention, therefore, is to improve on the prior art and to provide a method for preparing poly(hydroxymethyl)-functional siloxanes and silica gels, which ensures complete hydrolysis independently of silane concentration and solvent.

DETAILED DESCRIPTION OF THE PREFERRED EMBODIMENTS

The invention provides a method for preparing poly(hydroxymethyl)-functional siloxanes of the general formula I

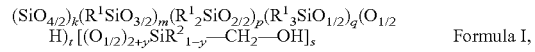

Formula I, which comprises reacting cyclic compounds having at least one unit of the general formula II

Formula II with water, wherein optionally one or more further hydrolyzable compounds of the general formula III

Formula III may be present, and wherein $R^1$ is a hydrogen atom or a cyclic or acyclic, linear or branched, aromatic or aliphatic or olefinic, saturated or unsaturated $C_1$-$C_{20}$ hydrocarbon residue or $C_1$-$C_{20}$ hydrocarbonoxy residue or $C_4$-$C_{40}$ polyether residue, each optionally substituted with $Q^1$, optionally interrupted by one or more groups $Q^2$ or comprising one or more groups $Q^2$, $R^2$ is a hydroxyl residue or a cyclic or acyclic, linear or branched, aromatic or aliphatic or olefinic, saturated or unsaturated $C_1$-$C_{20}$ hydrocarbon residue or $C_1$-$C_{20}$ hydrocarbonoxy residue or $C_4$-$C_{40}$ polyether residue or $Si_1$-$Si_{20}$ siloxanoxy residue, each optionally substituted with $Q^1$, optionally interrupted by one or more groups $Q^2$ or comprising one or more groups $Q^2$, $R^3$ is hydrogen or a cyclic or acyclic, linear or branched, aromatic or aliphatic or olefinic, saturated or unsaturated $C_1$-$C_{20}$ hydrocarbon residue or $C_4$-$C_{40}$ polyether residue or $Si_1$-$Si_{20}$ siloxanyl residue, each optionally substituted with $Q^1$, optionally interrupted by one or more groups $Q^2$ or comprising one or more groups $Q^2$, $Q^1$ is a heteroatom-containing monovalent residue, $Q^2$ is a heteroatom-containing divalent residue or a heteroatom-containing trivalent residue, Y is a hydrolyzable group attached to the silicon via a heteroatom, k, m, p, q and t are greater than or equal to zero, s and n are greater than zero, y is 0 or 1, and z is 0, 1, 2 or 3.

If compounds comprising units of the general formula II are hydrolyzed, i.e. suitable cyclic alkoxysilanes, optionally in the presence of hydrolyzable compounds of the formula III, then poly(hydroxymethyl)-functional siloxanes are surprisingly readily and specifically formed in good yields.

The term "poly(hydroxymethyl)-functional siloxanes" also includes polysiloxanes, polysiloxane resins and silica gels.

Compounds having at least one unit of the general formula II are referred to below simply as "compounds of the formula II".

The units $(SiO_{4/2})$, $(R^1SiO_{3/2})$ and $(R^1_2SiO_{2/2})$ in formula I may also occur repeatedly, for example, as blocks, as individual units or as alternating units.

The units $(R^1_3SiO_{1/2})$, $[(O_{1/2})_{2+y}SiR^2_{1-y}-CH_2-O-H]$ and $[O_{1/2}H]$ in formula I may occur, for example, at multiple sites on the polymer backbone, regularly or randomly distributed for example.

The variable y in compounds of the general formula I can have a different value in each of the s segments $[(O_{1/2})_{2+y}SiR^2_{1-y}-CH_2-OH]$.

The units $[SiR^2(OR^3)-CH_2-O]$ in formula II may also occur repeatedly, for example, as blocks, as individual units or as alternating units, where $R^2$ and $R^3$ do not have the same meaning in all units.

In the method according to the invention, the compounds of the formulae II and III or mixtures comprising these compounds, and also water, may be prepared, mixed and added to one another in any sequence, optionally also repeatedly, optionally also alternately. In the method according to the invention at least one compound of the formula II is used; two or more compounds of the formula II may also be used, simultaneously or sequentially, optionally also repeatedly, optionally also alternately. Optionally, one, two, three, four, five, six or more compounds of the formula III may additionally be used, simultaneously or sequentially, optionally also repeatedly, optionally also alternately. In the method according to the invention, at least one poly(hydroxymethyl)-functional siloxane of the formula I is prepared; two or more compounds of the formula I may also be prepared in parallel. The ratio of k, m, p, q, t and s to one another is in this case governed by the amounts of compounds of the formulae II and III used.

If compounds of the formula II are reacted with compounds of the formula III in a different quantitative ratio to that required for compounds of the formula I, then deficient components may subsequently be added at a later time point in any sequence, optionally in multiple portions, until the desired quantitative ratio is reached.

For complete hydrolysis, compounds of the formula II require 1 mol of water per mole of [$SiR^2(OR^3)$—$CH_2$—$O$] units if $R^2$ is not hydrolyzable and 1.5 mol of water if $R^2$ is a hydrolyzable residue. For complete hydrolysis, compounds of the formula III require 0.5 mol, 1 mol, 1.5 mol or 2 mol of water, if z=0, 1, 2 or 3 respectively, per mole of $R^1_{3-z}SiY_{1+z}$. If less than the stoichiometrically required amount of water is used, only partially hydrolyzed products are formed. In the method according to the invention, preferably at least the required amount of water for complete hydrolysis is used, preferably more than the required amount.

Alcohols $R^3OH$ and also, if appropriate, alcohols $R^2H$, are formed as by-products in the hydrolysis from the $OR^3$ groups and, if appropriate, from the $R^2$ groups, if $R^2$ is a hydrolyzable group, which remain in the reaction mixture or may be removed therefrom, by distillation for example.

Compounds YH are formed in the hydrolysis from the Y groups of the compounds of the formula III, and remain in the reaction mixture or may be removed therefrom, by distillation for example. If YH is an acid, it can be neutralised by addition of a base. The reaction product formed, a salt for example, can remain in the reaction mixture or may be removed therefrom, for example, by extraction or filtration. The base can be added before, during or after the hydrolysis reaction. If YH is a base, it can be neutralised by addition of an acid. The reaction product formed, a salt for example, may remain in the reaction mixture or may be removed therefrom, for example, by extraction or filtration. The acid may be added before, during or after the hydrolysis reaction.

The method according to the invention differs in this way from the known methods to date for preparing poly(hydroxymethyl)-functional siloxanes and silica gels. In the methods known to date for preparing poly(hydroxymethyl)-functional siloxanes, siloxanes are used or generated as precursors which bear a moiety of the structure siloxane-$CH_2$-A. Group A in this case is an acyloxy residue or a halogen atom and is converted to OH groups under harsh conditions, for example with alkali metal hydroxides (A=halogen) or with alcohols under acid catalysis or with borohydrides (A=acyloxy). The harsh reaction conditions frequently result in rearrangements of the siloxane skeleton or in unwanted subsequent reactions on the hydroxymethyl groups produced, such as cleavage of Si—C bonds. In the method according to the invention in contrast, it is possible to prepare poly(hydroxymethyl)-functional siloxanes surprisingly readily, under mild conditions and without subsequent reactions on the hydroxymethyl groups produced. In the known methods to date for preparing poly(hydroxymethyl)-functional silica gels, hydroxymethyltrialkoxysilanes are used which are present in oligomerized or polymeric form at high concentration such that complete hydrolysis is not guaranteed. In addition, an alcohol is required, at least as the predominant solvent. In the method according to the invention in contrast, it is possible to prepare fully hydrolyzed poly(hydroxymethyl)-functional silica gels surprisingly readily and under mild conditions.

The poly(hydroxymethyl)-functional siloxanes generated in the method according to the invention may still comprise silanol groups. These may be reacted with silylating agents, for example, according to a method described in DE 102009046254, in which low-silanol-content or silanol-free poly(hydroxymethyl)-functional siloxanes are formed. They may also be reacted, according to another method described in DE 102009046254, to give further terminal hydroxymethyl groups, such that low-silanol-content or silanol-free, predominantly or exclusively hydroxymethyl-functionalized poly(hydroxymethyl)-functional siloxanes can be generated. This can also be done at the same time as, or before, carrying out the method according to the invention. For this purpose, the compounds of the formula II used may also comprise [$SiR^2_2$—$CH_2$—$O$] units, which result in terminal hydroxymethyl groups.

The invention further relates to poly(hydroxymethyl)-functional siloxanes of the general formula Ia $(SiO_{4/2})_k(R^1SiO_{3/2})_m(R^1_2SiO_{2/2})_p(R^1_3SiO_{1/2})_u[O_{1/2}H]_v(O_{1/2}SiR^{22}_2$—$CH_2$—$OH)_l[(O_{1/2})_{2+y}SiR^2_{1-y}$—$CH_2$—$OH]_s$ 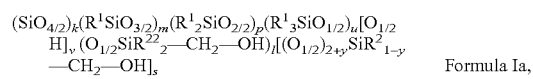

wherein
$R^1, R^2, Q^1, Q^2, k, m, p, y$ and s may have meanings and values as defined above,
$R^{22}$ is a cyclic or acyclic, linear or branched, aromatic or aliphatic or olefinic, saturated or unsaturated $C_1$-$C_{20}$ hydrocarbon residue or $C_1$-$C_{20}$ hydrocarbonoxy residue or $C_4$-$C_{40}$ polyether residue, each optionally substituted with $Q^1$, optionally interrupted by one or more groups $Q^2$ or comprising one or more groups $Q^2$,
l is greater than zero, and
u and v are greater than or equal to zero, and the ratio of s to the sum of k, m, p, and u is in the range from 1:10,000 to 10,000:1.

The variable y in compounds of the general formula Ia can have a different value in each of the s segments [$(O_{1/2})_{2+y}SiR^2_{1-y}$—$CH_2$—$OH$].

Compounds of the formula Ia arise from compounds of the formula I, in which in at least some of the segments ($R^1_3SiO_{1/2}$) two $R^1$ residues are $R^{22}$ and one $R^1$ residue is hydroxymethyl, q has the value u and t has the value v.

$R^1, R^2, Q^1, Q^2, k, m, p, y$ and s in compounds of the formula Ia have the preferred, more preferred or particularly preferred meanings described as preferred, more preferred or particularly preferred in compounds of the formula I. $R^{22}$ has the preferred, more preferred or particularly preferred meanings described as preferred, more preferred or particularly preferred for $R^2$.

u, v and l respectively have the preferred, more preferred or particularly preferred meanings described as preferred, more preferred or particularly preferred for q, t and s respectively.

The method according to the invention provides the option to prepare poly(hydroxymethyl)-functional siloxanes under mild conditions. Furthermore, it has the advantage that the degree of functionalization can be adjusted over a wide range in a freely selectable manner, such that, for example, the preparation of siloxanes having a certain number of SiCH$_2$OH groups is possible. These (poly)siloxanes are particularly well-suited to polyaddition reactions of the A-A+B-B type ("A"=SiCH$_2$OH, "B"=e.g. isocyanate). In this manner, the hydrophilicity of the siloxanes can also be regulated.

$R^1$, $R^2$ and $R^3$ preferably have 1 to 12 carbon atoms, more preferably 1 to 6 carbon atoms, preferably only carbon atoms and hydrogen atoms, or an alkoxy oxygen atom and otherwise only carbon atoms and hydrogen atoms.

$R^1$ and $R^2$ are preferably straight-chain or branched or cyclic $C_1$-$C_6$ hydrocarbon residues or $C_1$-$C_6$ hydrocarbonoxy residues. $R^3$ is preferably a straight-chain or branched or cyclic $C_1$-$C_6$ hydrocarbon residue. $R^1$ residues are preferably methyl, ethyl, phenyl, allyl and vinyl, more preferably methyl. $R^2$ residues are preferably methyl, ethyl, phenyl, allyl, vinyl, methoxy and ethoxy, more preferably methyl, methoxy and ethoxy. $R^3$ residues are preferably methyl, ethyl, n-propyl, isopropyl, n-butyl, sec-butyl, isobutyl, tert-butyl and phenyl, more preferably methyl and ethyl.

Preference is given to preparing compounds of the general formula I in which $R^1$ and $R^2$ are methyl residues. Preference is given to using compounds of the general formula II in which $R^2$ are methyl, methoxy or ethoxy residues and $R^3$ are methyl or ethyl residues. Preference is given to using compounds of the general formula III in which $R^1$ are methyl residues.

$Q^1$ is preferably a fluorine, chlorine, bromine, iodine, cyanato, isocyanato, silyl, silylalkyl, silylaryl, siloxy, siloxanoxy, siloxyalkyl, siloxanoxyalkyl, siloxyaryl, siloxanoxyaryl, hydroxyl, alkoxy, aryloxy, acyloxy, thiolato, amino, alkylamino, arylamino, dialkylamino, diarylamino, arylalkylamino, acylamino, imido, imino, O-alkyl-N-carbamato, O-aryl-N-carbamato, N-alkyl-O-carbamato, N-aryl-O-carbamato, hydroxycarbonyl, alkoxycarbonyl, aryloxycarbonyl or cyclic or acyclic carbonato, alkylcarbonato or arylcarbonato substituent.

$Q^2$ is preferably a heteroatom-containing divalent residue —O—, —S—, —N(R$^4$)—, —C(O)—, epoxy, —C(O)—O—, —O—C(O)—O—, —O—C(O)—N(R$^4$)—, —C(O)—N(R$^4$)—, —N[C(O)R$^4$]—, silanediyl, siloxanediyl or siloxanoxydiyl, where $R^4$ is hydrogen or optionally substituted $C_1$-$C_{20}$-alkyl or $C_6$-$C_{20}$-aryl residues, or a heteroatom-containing trivalent residue such as —N= or —P=.

Y is preferably a fluorine, chlorine, bromine, iodine, hydroxyl, alkoxy, aryloxy, acyloxy, acyl, thiolato, amino, alkylamino, arylamino, dialkylamino, diarylamino, arylalkylamino, acylamino, silylamino, imido, imino, cyano, cyanato, isocyanato, O-alkyl-N-carbamato, O-aryl-N-carbamato, N-alkyl-O-carbamato, N-aryl-O-carbamato, hydroxycarbonyl, alkoxycarbonyl, aryloxycarbonyl or cyclic or acyclic carbonato, alkylcarbonato or arylcarbonato substituent, particularly a hydroxyl group, alkoxy group, acyloxy group, optionally substituted amino group and chlorine.

The variable n in formula II preferably has values greater than or equal to 2, more preferably values from 2 to 100, and yet more preferably from 2 to 30, particularly from 2 to 10. The variable n can have, for example, the values 2, 3, 4, 5, 6, 7, 8, 9, 10 or 11-30 or greater. The cyclic compounds of the formula II may comprise further [SiR$^2$(OR$^3$)—CH$_2$—O] units in the residues $R^2$ or $R^3$.

The poly(hydroxymethyl)-functional siloxane of the general formula I may be, for example, linear, cyclic or branched. It may be present in a monomodal, bimodal or multimodal molar mass distribution and at the same time the molar mass distribution can be narrow or very broad.

In one preferred variant of a poly(hydroxymethyl)-functional siloxane, the variables k, m, p and q are zero, so that the compound I consists only of [(O$_{1/2}$)$_{2+y}$SiR$^2_{1-y}$—CH$_2$—OH] units with $R^2$, y and s as defined above. The variable s in this case is preferably a number from 2 to 100,000, preferably from 2 to 10,000, more preferably from 2 to 1000. The ratio of t to s is preferably less than or equal to 2, more preferably less than or equal to 1, and particularly zero.

In another preferred variant of a poly(hydroxymethyl)-functional siloxane, the ratio of s to the sum of k, m, p and q is preferably in the range from 1:10,000 to 10,000:1, preferably in the range from 1:1000 to 1000:1, more preferably in the range from 1:100 to 100:1. The ratio of t to s in this case is preferably in the range from 0 to 10,000:1, more preferably in the range from 0 to 1000:1, and most preferably in the range from 0 to 100:1, while t can, in particular, be equal to zero. The variable s is preferably a number from 2 to 100,000, more preferably 2 to 10,000, and most preferably 2 to 1000.

The poly(hydroxymethyl)-functional silica gel of the general formula I may be, for example, solid, porous, amorphous or crystalline, and may be obtained as, for example, shaped bodies, gels, films, membranes, particles, nanoparticles or sols. In the case of porous products, the pore sizes thereof may have a monomodal, bimodal or multimodal distribution, and may at the same time have a narrow or very broad pore size distribution. In the case of particles or nanoparticles, the particle size distribution may be monomodal, bimodal or multimodal, and may at the same time have a narrow or very broad particle size distribution.

In one preferred variant of a poly(hydroxymethyl)-functional silica gel, the variables k, m, p and q are zero, such that the compound I consists only of [(O$_{1/2}$)$_{2+y}$SiR$^2_{1-y}$—CH$_2$—OH] units with $R^2$, y and s as defined above. In this case y is preferably equal to 1. The ratio of t to s is preferably less than or equal to 2, more preferably less than or equal to 1, and most preferably zero.

In another preferred variant of a poly(hydroxymethyl)-functional silica gel, the ratio of s to the sum of k, m, p and q is preferably in the range from 1:10,000 to 10,000:1, more preferably in the range from 1:1000 to 1000:1, and most preferably in the range from 1:100 to 100:1. The ratio of t to s in this case is preferably in the range from 0 to 10,000:1, more preferably in the range from 0 to 1000:1, and most preferably in the range from 0 to 100:1, while in particular t can be equal to 0.

All the numbers, sums and ratios cited refer to the number of monomer units present in the product.

A preferred method for preparing poly(hydroxymethyl)-functional siloxanes is characterized in that the compounds used having at least one unit of the formula II are the compounds 1 to 6 below:

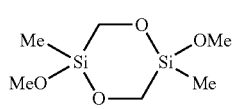

1

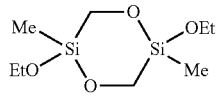

2

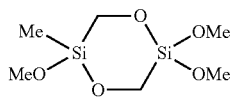

3

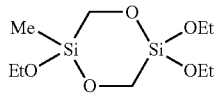

4

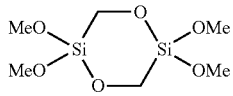

5

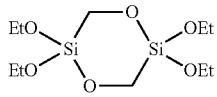

6

Compounds of the formula II, particularly the compounds 1-6, may be prepared by metal-catalyzed transesterification with elimination of a low molecular weight ester from suitable (acyloxymethyl)alkoxysilanes (DE 102010003108).

A preferred method for preparing poly(hydroxymethyl)-functional siloxanes is characterized in that the additional hydrolyzable compounds of the formula III are compounds of the formula IIIa below $$R^{11}{}_{3-z}Si(OR^5)_{1+z}$$ Formula IIIa wherein $R^{11}$ is methyl, ethyl, vinyl, allyl or phenyl and $R^5$ is methyl, ethyl, n-propyl, isopropyl, n-butyl, isobutyl, sec-butyl, tert-butyl, formyl or acetyl and z has values as defined above.

$R^{11}$ is preferably methyl, ethyl, vinyl or phenyl, more preferably methyl or vinyl, and most preferably methyl.

$R^5$ is preferably methyl, ethyl, n-propyl, n-butyl or acetyl, more preferably methyl, ethyl or acetyl, and most preferably methyl or acetyl.

The abovementioned methods may preferentially be carried out at temperatures from −100° C. to 200° C., more preferably from 0° C. to 100° C., yet more preferably from 0° C. to 50° C., and particularly from 0° C. to 30° C. The method may be carried out either uncatalyzed or catalyzed.

The catalyst preferably used in this case is an inorganic or organic Brønsted acid or Brønsted base or an inorganic or organic Lewis acid or Lewis base.

The acids preferably used are carboxylic acids, partially esterified carboxylic acids, particularly monocarboxylic acids, preferably formic acid or acetic acid, non-esterified or partially esterified mono-, oligo- or polyphosphoric acids, sulfonic acids, alkyl hydrogen sulfates or acidic ion exchangers. Preferred bases used are preferably ammonia, amines, guanidines, amidines, alkylammonium hydroxides or metal hydroxides.

The catalysts used may remain in the reaction mixture following the hydrolysis or be removed therefrom, for example, by distillation, extraction, decanting, filtration, centrifugation, adsorption or precipitation. They may also be chemically or physically deactivated after the reaction, for example, by complexation, neutralisation or heat. The deactivation product may remain in the reaction mixture or be removed therefrom, for example, by the methods just mentioned. Examples of catalysts which may be removed by distillation are carboxylic acids, such as formic acid or acetic acid, or ammonia, amine bases, amidine bases or guanidine bases, such as triethylamine, tributylamine, ethyldiisopropylamine, ethylenediamine, tetramethylguanidine, 1,8-diazabicyclo[5.4.0]undec-7-ene, 1,5-diazabicyclo[4.3.0]non-5-ene or 1,4-diazabicyclo[2.2.2]octane. Examples of catalysts which may be removed by decanting, filtration or by centrifugation are heterogeneous catalysts such as polymer-supported acids or bases, acidic or basic ion exchangers, or acidic or basic aluminum oxide. Preference is given to using catalysts which can be easily removed from the reaction mixture, for example, by distillation (optionally under reduced pressure), extraction or filtration.

The method can be carried out both with and without the use of solvents, namely either monophasic or polyphasic, for example as a dispersion hydrolysis. In this case, the method is carried out optionally under reduced pressure or elevated pressure or at atmospheric pressure (0.1 MPa absolute). The method may be carried out continuously or as a batch process.

The solvents used can be, for example, cyclic or acyclic hydrocarbons, ethers, esters, alcohols, amides, urea derivatives or halogenated organic compounds or solvent mixtures. Preference is given to using inert solvents, particularly aprotic solvents, such as aliphatic hydrocarbons such as heptane, and aromatic hydrocarbons such as toluene. Ethers such as tetrahydrofuran, diethyl ether or methyl tert-butyl ether may likewise be used. Preference is given to solvents or solvent mixtures having a boiling point or boiling point range of up to 120° C. at 0.1 MPa absolute.

The method according to the invention may be carried out in the presence of one or more surface-active substances. These substances have a structure-conferring effect by the formation of supramolecular structures, micelles for example, particularly in the preparation of poly(hydroxymethyl)-functional silica gels. In particular, the morphology of particles or pores may be influenced, for example, by a template effect. Both anionic and cationic or non-ionic surface-active substances can be used. Examples of anionic surface-active substances are alkyl sulfonates, e.g. sodium bis-2-ethylhexyl sulfosuccinate (AOT), salts of alkyl sulfate esters, e.g. sodium dodecyl sulfate or alkylbenzene sulfonates. Examples of non-ionic surface-active substances are polyethylene glycol monoether or fatty acid esters of polyethers, polyalcohols and sugars. Examples of cationic surface-active substances are quarternary ammonium salts, e.g. hexadecyltrimethylammonium bromide or dimethyldioctadecylammonium chloride.

The poly(hydroxymethyl)-functional siloxanes prepared according to one of the abovementioned methods may be used for reaction with isocyanates, for preparing urethanes, polyurethanes or polyurethane copolymers, for reaction with carboxylic acids or with carboxylic acid derivatives, or for preparing esters, polyesters or polyester copolymers. At a sufficiently high degree of functionalization, subsequent reactions on the poly(hydroxymethyl)-functional siloxanes may be carried out in water or water-containing solvents, since these substances are water-soluble or readily dispersible in water. The poly(hydroxymethyl)-functional siloxanes may be further used to coat surfaces. This may be carried out either during or after the implementation of the method according to the invention.

The meanings of all aforementioned symbols of the aforementioned formulae are each mutually independent, unless explicitly stated otherwise.

In the examples below, all pressures are 0.10 MPa (abs.) and all temperatures are 20° C., unless stated otherwise.

Example 1

Preparation of a Compound of the General Formula I

Uncatalyzed hydrolysis of 2,5-dimethoxy-2,5-dimethyl-1,4-dioxa-2,5-disilacyclohexane 5.2 g (25 mmol) of 2,5-dimethoxy-2,5-dimethyl-1,4-dioxa-2,5-disilacyclohexane (1) were dissolved in 10 mL of methanol, admixed with 1 mL (1.0 g, 55.5 mmol) of water and the mixture was stirred at room temperature. After 1.5 h the and $^{29}$Si-NMR spectrum showed complete conversion. The solvent and excess water were removed on a rotary evaporator. 4.6 g (100%) of a colorless, elastic solid remained which was only soluble in water, methanol and DMSO. According to the mass spectrum the solid consisted of cyclic and linear oligomers of [—Si(CH$_3$)(CH$_2$OH)O—]$_s$ with s=4 to 21.

$^1$H-NMR (DMSO-d$_6$): 0.14 ppm (broad, 3H, Si—CH$_3$), 3.09+3.3 . . . 3.5 Ppm (broad, 2H, Si—CH$_2$—O), 4.22 ppm (t/broad, 1H, OH)

$^{13}$C-NMR (DMSO-d$_6$): −0.5 . . . −1.0 ppm (broad, 1C, Si—CH$_3$), 53.7 . . . 54.0 Ppm (broad, 1C, Si—CH$_2$—OH)

$^{29}$Si-NMR (DMSO-d$_6$): −19.5 . . . −20.5 ppm (s, >6 x, cyclen, 29%), −21.0 . . . −23.0 ppm (s, >10 x, some broad, linear compounds, 71%)

Example 2

Preparation of a Compound of the General Formula I

Base-catalyzed hydrolysis of 2,2,5,5-tetramethoxy-1,4-dioxa-2,5-disilacyclohexane A mixture of 0.40 g (22.1 mmol) of water, 1.50 mL (20.0 mmol NH$_3$, 56.6 mmol H$_2$O) of a 25% ammonia solution and 94 mL of methanol were degassed in an ultrasound bath with introduction of argon. 4.38 g (18.2 mmol) of 2,2,5,5-tetramethoxy-1,4-dioxa-2,5-disilacyclohexane (5) were slowly added dropwise to the solution. The reaction mixture was stirred for 1 day at RT. The white solid thus obtained (2.39 g, 79%) was filtered off, washed with methanol and dried under reduced pressure.

Elemental analysis: C, 12.26%; H, 3.70%; Si, 40.49%;
Solid-state $^{13}$C-NMR: 51.0 ppm (CH$_2$, very sharp peak)
Solid-state $^{29}$Si-NMR: −75.2 ppm (~90%, O$_{3/2}$SiCH$_2$OH), −66.4 ppm (shoulder, ~10%, (HO)O$_{2/2}$SiCH$_2$OH)
Surface area (BET): 132 m$^2$/g
Average particle size (light scattering): 296 nm

Example 3

Preparation of a Compound of the General Formula I

Base-catalyzed dispersion hydrolysis of 2,2,5,5-tetramethoxy-1,4-dioxa-2,5-disilacyclohexane A water-in-oil microemulsion was prepared by degassing 1.67 g (3.74 mmol) of sodium 1,2-bis(2-ethylhexyloxycarbonyl)-1-ethanesulfonate (AOT), 0.45 g (24.96 mmol) of water, 4.67 mg (83.2 μmol) of potassium hydroxide and 7.5 g (74.9 mmol) of n-heptane in an ultrasound bath with introduction of argon and mixing the substances in the process. A clear, transparent solution was produced which was stable over at least several hours. 1.00 g (4.16 mmol) of 2,2,5,5-tetramethoxy-1,4-dioxa-2,5-disilacyclohexane (5) was added dropwise to this solution. The reaction mixture was stirred for 14 h at room temperature. The precipitated white solid was then homogenized and suspended in the ultrasound bath and was then filtered off and washed repeatedly with heptane and ethanol. The white solid (562 mg, 81%) was dried under reduced pressure.

Elemental analysis: C, 13.84%; H, 3.79%; Si, 32.06%; ~> [(HO)$_{0.3}$O$_{2.7/2}$SiCH$_2$OH]
Solid-state $^{13}$C-NMR: 51.4 ppm (CH$_2$, very sharp peak)
Solid-state $^{29}$Si-NMR: −75.5 ppm (~90%, O$_{3/2}$SiCH$_2$OH), −65.8 ppm (shoulder, ~10%, (HO)O$_{2/2}$SiCH$_2$OH)
Surface area (BET): 298 m$^2$/g
Average particle size (light scattering): 524 nm

Example 4

Preparation of a Compound of the General Formula I

Uncatalyzed co-hydrolysis of 2,5-dimethoxy-2,5-dimethyl-1,4-dioxa-2,5-disilacyclohexane and dimethoxydimethylsilane 5.2 g (25 mmol) of 2,5-dimethoxy-2,5-dimethyl-1,4-dioxa-2,5-disilacyclohexane (1) and 6.0 g (50 mmol) of dimethoxydimethylsilane were dissolved in 40 ml of methanol, admixed with 2 ml (2.0 g, 111 mmol) of water and the mixture was stirred at room temperature. After 1 day the $^1$H-NMR spectrum showed complete conversion. The solvent and excess water were removed on a rotary evaporator. 8.1 g (99%) of a colorless viscous liquid remained, which was freely soluble in water, DMSO, MeOH, EtOH, diethylether, THF, acetone, CH$_2$Cl$_2$, CHCl$_3$ and acetonitrile and poorly soluble in toluene. According to the mass spectrum the liquid consisted of cyclic and linear oligomers of [—Si(CH$_3$)$_2$O—]$_p$ [—Si(CH$_3$)(CH$_2$OH)O-]$_s$ with p+s=4 to at least 18 and s=2 to (p+s).

$^1$H-NMR (CDCl$_3$): 0.1 . . . 0.2 ppm (broad, 9H, Si—CH$_3$), 3.3+3.45 . . . 3.6 ppm (broad, 2H, Si—CH$_2$—O)

$^{13}$C-NMR (CDCl$_3$): −5 . . . −4+−3 . . . −1.5+−0.5 . . . 1 ppm (broad, 3C, Si—CH$_3$), 52.5 . . . 53+53.5 . . . 54.5 ppm (broad, 1C, Si—CH$_2$—OH)

$^{29}$Si-NMR (CDCl$_3$): −30 . . . −25 ppm (SiMe(CH$_2$OH)O, broad, 45%), −23 . . . −15 ppm (SiMe$_2$O+SiMe(CH$_2$OH)O, broad, 18%), −12 . . . −6 ppm (SiMe$_2$O, broad, 32%), −5 . . . 5 ppm (some broad, 5%)

Viscosity: 121.8 mPa*s

Example 5

Preparation of a Compound of the General Formula I

Base-catalyzed hydrolysis of 2,2,5,5-tetramethoxy-1,4-dioxa-2,5-disilacyclohexane and tetramethylorthosilicate (TMOS)

A mixture of 0.92 g (50.9 mmol) of water, 0.75 mL (10.0 mmol NH$_3$, 28.3 mmol H$_2$O) of 25% ammonia solution and 94 mL of methanol were degassed in an ultrasound bath with introduction of argon. 2.58 g (16.9 mmol) of TMOS were added dropwise to the solution. The reaction solution was stirred for 1 day at room temperature. For functionalizing the silica particles, 3.06 g (12.7 mmol) of 2,2,5,5-tetramethoxy-1,4-dioxa-2,5-disilacyclohexane (5) were slowly added dropwise. The mixture was stirred for 2 days at room temperature.

The precipitated white solid was filtered off, washed with methanol and subsequently dried under reduced pressure (3.14 g, 100%).

Elemental analysis: C, 9.36%; H, 3.00%; Si, 35.48%; ~> [(HO)$_{0.53}$O$_{2.47/2}$SiCH$_2$OH+0.62 (HO)$_{0.53}$SiO$_{3.47/2}$]

Solid-state $^{13}$C-NMR: 51.0 ppm (CH$_2$, very sharp peak)

Solid-state $^{29}$Si-NMR: −75.1 ppm (~50%, O$_{3/2}$SiCH$_2$OH), −66.1 ppm (shoulder, ~10%, (HO)O$_{2/2}$SiCH$_2$OH) −110.9 ppm (~30%, SiO$_{4/2}$), −104.0 ppm (shoulder, ~10%, (HO)SiO$_{3/2}$)

Surface area (BET): 470 m$^2$/g

Average particle size (light scattering): 90% 30 nm, 10% 145 nm

Example 6

Preparation of a Compound of the General Formula I

Base-catalyzed dispersion hydrolysis of 2,2,5,5-tetramethoxy-1,4-dioxa-2,5-disilacyclohexane and tetraethylorthosilicate (TEOS)

A water-in-oil microemulsion was prepared by degassing 10.0 g (22.5 mmol) of sodium 1,2-bis(2-ethylhexyloxycarbonyl)-1-ethanesulfonate (AOT), 2.50 g (138.8 mmol) of water, 0.5 mL (6.61 mmol NH$_3$, 18.9 mmol H$_2$O) of 25% ammonia solution and 57.8 mL of toluene in an ultrasound bath with introduction of argon and mixing the substances in the process. A clear, transparent solution was formed, which was stable over several hours. 0.95 g (4.56 mmol) of TEOS was added dropwise to this solution and the reaction mixture was stirred for 1 day at room temperature. 0.83 g (3.46 mmol) of 2,2,5,5-tetramethoxy-1,4-dioxa-2,5-disilacyclohexane (5) was then added dropwise. After stirring for 1 day, the colloidal silica particles were centrifuged, washed twice with toluene and dried under reduced pressure. The white solid (691 mg, 81%) was soluble in water.

Solid-state $^{13}$C-NMR: 55.3 ppm (CH$_2$, very sharp peak)

Solid-state $^{29}$Si-NMR: −75.3 ppm (O$_{3/2}$SiCH$_2$OH), −66.6 ppm (shoulder, (HO)O$_{2/2}$SiCH$_2$OH) −110.5 ppm (SiO$_{4/2}$), −100.5 ppm (shoulder, (HO)SiO$_{3/2}$)

Surface area (BET): 72 m$^2$/g

Average particle size (light scattering): 42% 44 nm, 58% 287 nm

The invention claimed is:

1. A method for preparing poly(hydroxymethyl)-functional siloxanes of the formula I (SiO$_{4/2}$)$_k$(R$^1$SiO$_{3/2}$)$_m$(R$^1{}_2$SiO$_{2/2}$)$_p$(R$^1{}_3$SiO$_{1/2}$)$_q$(O$_{1/2}$H)$_t$ [(O$_{1/2}$)$_{2+y}$SiR$^2{}_{1-y}$—CH$_2$—OH]$_s$     Formula I, comprising reacting cyclic compounds having at least one unit of the formula II

[SiR$^2$(OR$^3$)—CH$_2$—O]$_n$     Formula II with water, wherein optionally one or more hydrolyzable compounds of the formula III R$^1{}_{3-z}$SiY$_{1+z}$     Formula III may be present, wherein R$^1$ is hydrogen, a cyclic or acyclic, linear or branched, aromatic, aliphatic or olefinic, saturated or unsaturated C$_1$-C$_{20}$ hydrocarbon residue, a C$_1$-C$_{20}$ hydrocarbonoxy residue, or a C$_4$-C$_{40}$ polyether residue, each optionally substituted with Q$^1$, optionally interrupted by one or more groups Q$^2$ or comprising one or more groups Q$^2$, R$^2$ is hydroxyl or a cyclic or acyclic, linear or branched, aromatic, aliphatic or olefinic, saturated or unsaturated C$_1$-C$_{20}$ hydrocarbon residue, C$_1$-C$_{20}$ hydrocarbonoxy residue, C$_4$-C$_{40}$ polyether residue, or Si$_1$-Si$_{20}$ siloxanoxy residue, each optionally substituted with Q$^1$, optionally interrupted by one or more groups Q$^2$ or comprising one or more groups Q$^2$, R$^3$ is hydrogen or a cyclic or acyclic, linear or branched, aromatic, aliphatic, olefinic, saturated or unsaturated C$_1$-C$_{20}$ hydrocarbon residue, a C$_4$-C$_{40}$ polyether residue, or a Si$_1$-Si$_{20}$ siloxanyl residue, each optionally substituted with Q$^1$, optionally interrupted by one or more groups Q$^2$ or comprising one or more groups Q$^2$, Q$^1$ is a heteroatom-containing monovalent residue, Q$^2$ is a heteroatom-containing divalent residue or a heteroatom-containing trivalent residue, Y is a hydrolyzable group attached to silicon via a heteroatom, k, m, p, q and t are greater than or equal to zero, s and n are greater than zero, y is 0 or 1, and z is 0, 1, 2 or 3.

2. The method of claim 1, wherein R$^1$ and R$^2$ are straight-chain or branched or cyclic C$_1$-C$_6$ hydrocarbon residues or C$_1$-C$_6$ hydrocarbonoxy residues and R$^3$ is a straight-chain or branched or cyclic C$_1$-C$_6$ hydrocarbon residue.

3. The method of claim 1, wherein the compounds having at least one unit of the formula II are selected from compounds 1 to 6

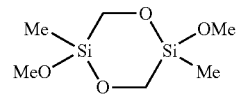

1

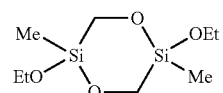

2

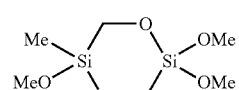

3

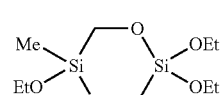

4

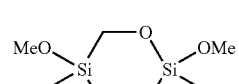

5

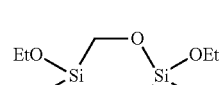

6

4. The method of claim 2, wherein the compounds having at least one unit of the formula II are selected from compounds 1 to 6

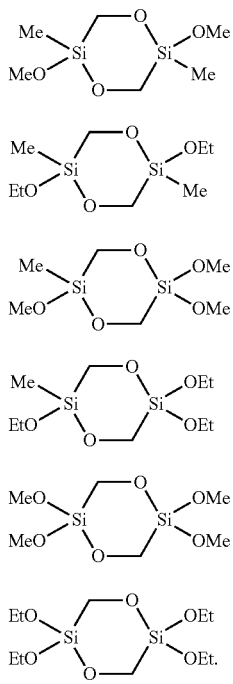

5. The method of claim 1, wherein compounds of the formula IIIa $$R^{11}{}_{3-z}Si(OR^5)_{1+z}$$ Formula IIIa are used as additional hydrolyzable compounds of the formula III, wherein
$R^{11}$ is methyl, ethyl, vinyl, allyl or phenyl and
$R^5$ is methyl, ethyl, n-propyl, isopropyl, n-butyl, isobutyl, sec-butyl, tert-butyl, formyl or acetyl.

6. The method of claim 2, wherein compounds of the formula IIIa $$R^{11}{}_{3-z}Si(OR^5)_{1+z}$$ Formula IIIa are used as additional hydrolyzable compounds of the formula III, wherein
$R^{11}$ is methyl, ethyl, vinyl, allyl or phenyl and
$R^5$ is methyl, ethyl, n-propyl, isopropyl, n-butyl, isobutyl, sec-butyl, tert-butyl, formyl or acetyl.

7. The method of claim 3, wherein compounds of the formula IIIa $$R^{11}{}_{3-z}Si(OR^5)_{1+z}$$ Formula IIIa are used as additional hydrolyzable compounds of the formula III, wherein
$R^{11}$ is methyl, ethyl, vinyl, allyl or phenyl and
$R^5$ is methyl, ethyl, n-propyl, isopropyl, n-butyl, isobutyl, sec-butyl, tert-butyl, formyl or acetyl.

8. The method of claim 4, wherein compounds of the formula IIIa $$R^{11}{}_{3-z}Si(OR^5)_{1+z}$$ Formula IIIa are used as additional hydrolyzable compounds of the formula III, wherein
$R^{11}$ is methyl, ethyl, vinyl, allyl or phenyl and
$R^5$ is methyl, ethyl, n-propyl, isopropyl, n-butyl, isobutyl, sec-butyl, tert-butyl, formyl or acetyl.

9. The method of claim 1, wherein at least one catalyst which is an inorganic or organic Brønsted acid or Brønsted base or an inorganic or organic Lewis acid or Lewis base is present.

10. The method of claim 1, which is carried out in the presence of a surface-active substance.

11. The method of claim 1, which is conducted in the presence of one or more solvents.

12. The method of claim 1, which is carried out at 0° C. to 100° C.

13. The method of claim 1, in which poly(hydroxymethyl)-functional siloxanes of the formula I are prepared with k=m=p=q=0.

* * * * *